US009101325B2

(12) United States Patent
Wang et al.

(10) Patent No.: US 9,101,325 B2
(45) Date of Patent: Aug. 11, 2015

(54) CHEST RADIOGRAPHY IMAGE CONTRAST AND EXPOSURE DOSE OPTIMIZATION

(75) Inventors: Xiaohui Wang, Pittsford, NY (US); Zhimin Huo, Pittsford, NY (US); Samuel Richard, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 146 days.

(21) Appl. No.: 13/607,669

(22) Filed: Sep. 8, 2012

(65) Prior Publication Data

US 2013/0259352 A1 Oct. 3, 2013

Related U.S. Application Data

(60) Provisional application No. 61/616,455, filed on Mar. 28, 2012.

(51) Int. Cl.
*G06K 9/00* (2006.01)
*A61B 6/00* (2006.01)

(52) U.S. Cl.
CPC ................ *A61B 6/50* (2013.01); *A61B 6/5252* (2013.01); *A61B 6/542* (2013.01); *A61B 6/545* (2013.01); *A61B 6/4035* (2013.01); *A61B 6/4233* (2013.01)

(58) Field of Classification Search
None
See application file for complete search history.

(56) References Cited

U.S. PATENT DOCUMENTS

| | | | | |
|---|---|---|---|---|
| 7,085,407 | B2 | 8/2006 | Ozaki | |
| 2007/0019852 | A1 | 1/2007 | Schildkraut et al. | |
| 2008/0298666 | A1* | 12/2008 | Mysore Siddu et al. | 382/132 |
| 2009/0060366 | A1 | 3/2009 | Worell et al. | |
| 2009/0060372 | A1 | 3/2009 | Maton et al. | |
| 2009/0190818 | A1 | 7/2009 | Huo | |
| 2009/0214099 | A1* | 8/2009 | Merlet | 382/132 |
| 2009/0290779 | A1 | 11/2009 | Knapp et al. | |
| 2010/0027867 | A1* | 2/2010 | Bernhardt et al. | 382/132 |
| 2011/0311026 | A1* | 12/2011 | Lalena | 378/98.5 |

OTHER PUBLICATIONS

Suzuki et al., Image-Processing Technique for Suppressing Ribs in Chest Radiographs by Means of Massive Training Artificial Neural Network (MTANN), IEEE Transactions on Medical Imaging, vol. 25 No. 4, Apr. 2006, pp. 406-416.

Vogelsang et al., Detection and Compensation of Rib Structures in Chest Radiographs for Diagnose Assistance Proceedings of SPIE, 3338:pp. 774-785 (1998).

Vogelsang et al., Model based analysis of chest radiographs, Proceedings of SPIE 3979, pp. 1040-1052 (2000).

M. Loog, B. van Ginneken, A. M. R. Schilham, "Filter learning: Application to suppression of bony structures from chest radiographs", Medical Image Analysis, 10 (2006), pp. 826-840.

J. M. Boone et al., "A comparison of mono- and poly-energetic x-ray beam performance for radiographic and fluoroscopic imaging," Medical Physics, vol. 21, No. 12, 1994, pp. 1853-1863.

(Continued)

*Primary Examiner* — Siamak Harandi

(57) ABSTRACT

A method for obtaining a digital chest x-ray image of a patient. The method includes providing a default set of technique settings for the chest x-ray, wherein the default set is selectable by an operator command and includes using a peak kilovoltage exposure setting that is below 90 kVp with beam filtration of the x-ray, and applying a rib contrast suppression algorithm to the digital chest x-ray image data acquired from the exposure.

13 Claims, 14 Drawing Sheets

60 28 24 26 30 40 32 72 70 12 50 46 48

(56) References Cited

OTHER PUBLICATIONS

C. S. Moore, "Investigation of optimum X-ray beam tube voltage and filtration for chest radiography with a computed radiography system," The British Journal of Radiology, vol. 81, 2008, pp. 771-777.
F. Li et al, "Improved Detection of Subtle Lung Nodules by Use of Chest Radiographs with Bone Suppression Imaging: Receiver Operating Characteristic Analysis With and Without Localization," American Journal of Roentgenology, vol. 196, 2011, pp. W535-W541.
S. Oda et al, "Performance of Radiologists in Detection of Small Pulmonary Nodules on Chest Radiographs: Effect of Rib Suppression with a Massive-Training Artificial Neural Network," American Journal of Roentgenology, vol. 193, 2009, pp. W397-W402.
Commonly Assigned U.S. Appl. No. 13/527,629, entitled: Rib Suppression in Radiographic Images, filed Jun. 20, 2012, by Huo et al.

* cited by examiner

CHEST RADIOGRAPHY IMAGE CONTRAST AND EXPOSURE DOSE OPTIMIZATION

CROSS-REFERENCE TO RELATED APPLICATIONS

Priority is claimed from U.S. Provisional Ser. No. 61/616,455, filed Mar. 28, 2012 in the names of Xiaohui Wang et al. entitled "CHEST RADIOGRAPHY IMAGE CONTRAST AND EXPOSURE DOSE OPTIMIZATION", incorporated herein by reference in its entirety.

FIELD OF THE INVENTION

The invention relates generally to the field of radiographic imaging and more particularly to methods for improving image quality and exposure settings for radiographic images.

BACKGROUND OF THE INVENTION

The chest x-ray is used for detecting a number of patient conditions and for imaging a range of skeletal and organ structures. Radiographic images of the chest can be useful for detection of lung nodules and other features that indicate lung cancer and other pathologic structures. In clinical applications such as in the Intensive Care Unit (ICU), chest x-rays can have particular value for indicating pneumothorax as well as for tube/line positioning.

The chest region includes a range of tissues, from rib and other bone structures to the lung parenchyma. This can complicate the task of radiographic imaging for the chest region, since the different types of bone and tissue materials have different densities. Optimization techniques for chest imaging require making compromises to provide a suitable signal-to-noise (S/N) ratio and sufficient contrast for soft tissue.

Chest radiographs are used to examine the lung parenchyma, for which tissue/air contrast is an important feature. As indicated in published work either based on Monte Carlo simulations ("A comparison of mono- and poly-energetic x-ray beam performance for radiographic and fluoroscopic imaging," J. M. Boone et al., *Medical Physics*, Vol. 21, No. 12, 1994) or based on experimental measurements ("Investigation of optimum X-ray beam tube voltage and filtration for chest radiography with a computed radiography system," C. S. Moore, *The British Journal of Radiology*, Vol. 81, 2008), an identified kV (kVp) range for soft-tissue and air contrast, for average-sized adult patients, is 60 to 80 using poly-energetic x-ray beams. However, an x-ray exposure technique that is used for in-room posterior-anterior (PA) view chest radiography specifies 110 kVp to 130 kVp (such as given in *Bontrager's Pocket Atlas*, "Handbook of Radiographic Positioning and Techniques," Bontrager Publishing, Inc.). This higher kVp range is used because, in chest images, the bone contrast from the surrounding rib cage is reduced as much as possible to allow better visibility of the underlying tissue. The Monte Carlo simulation described by Boone et al. indicates that, with increasing exposure kVp, bone contrast decreases at a faster rate than soft tissue contrast decreases. Acquiring chest images at higher kVp helps to mitigate the bone contrast while maintaining a reasonable level of soft tissue contrast. However, the contrast of the lung parenchyma may be viewed as some as being less than optimal. This can complicate diagnosis and features may be misinterpreted.

Higher kVp levels for chest imaging relates to increased x-ray scatter. Scatter reduces image detail contrast and increases noise levels, both of which hinder diagnostic accuracy. X-ray anti-scatter grids are frequently used to reduce scattering, but have negative effects. Grids of higher ratios are required at higher energy levels, increasing the amount of incident exposure that is required to compensate the exposure loss, but at the expense of increased patient-absorbed dose.

A further problem relates to the need for imaging both bone and soft tissue in some patients. Studies by Boone et al. indicate that 50 kVp is an optimal setting for bone contrast. However, standard chest exams are performed at higher kVp, typically around 120 kVp, so that rib bone contrast is reduced in the images obtained, with correspondingly reduced bone detail conspicuity for diagnosis. Thus, patients for whom both thoracic bones and lung regions must be examined undergo two separate examinations, one radiograph taken at the 120 kVp level, another taken at 70 kVp. Because multiple views may be required, a patient may need to undergo more than two exposures for a chest exam, one set of exposures optimized for lung fields, the other optimized for thoracic bones. Thus, the need to image at two different kVp levels can directly translate to double or triple the exposure dose to the patient.

Recent work in rib contrast suppression has shown results that could help to diagnose lung nodules ("Improved Detection of Subtle Lung Nodules by Use of Chest Radiographs with Bone Suppression Imaging: Receiver Operating Characteristic Analysis With and Without Localization," F. Li et al, *American Journal of Roentgenology*, vol. 196, 2011, and "Performance of Radiologists in Detection of Small Pulmonary Nodules on Chest Radiographs: Effect of Rib Suppression with a Massive-Training Artificial Neural Network," S. Oda et al, *American Journal of Roentgenology*, vol. 193, 2009). As noted from the published images, both methods try to suppress the bone conspicuity completely. In reality, the bone suppression algorithm may not work perfectly; part of the rib bones may still not be sufficiently suppressed. The remaining rib edges may appear as fine lines across the lung field and may have appearance that is similar to pneumothorax, causing mis-diagnosis. Applicants have noted that it is desirable to mitigate this problem when rib contrast suppression is applied.

The use of lower energy x-ray photons helps to maximize soft-tissue and bone contrast in chest radiographs, but there can be negative effects if not applied appropriately. Lower energy photons become absorbed quickly by human tissues as the poly-energetic x-ray beam penetrates the patient. The negative impact of absorption is two-fold: 1) potentially increased patient-absorbed dose, and 2) "beam hardening" effects. Beam hardening essentially modifies the x-ray spectrum and reduces the effectiveness of radiation that is otherwise optimized for chest imaging. This effect becomes worse as patient size increases. Thus, lower energy radiation levels are avoided for chest x-ray imaging, even though these levels could provide improved imaging of soft tissues.

Thus, it can be seen that there is a need for improved methods for setting imaging parameters and image processing parameters that provide the optimal soft-tissue and bone contrast for chest radiography using a single x-ray exposure, and selectively present the anatomical information based on diagnostic purposes at the optimal patient dose efficiency.

SUMMARY OF THE INVENTION

Embodiments of the present invention address the need for improved imaging parameters and processing for chest x-rays. Advantageously, embodiments of the present invention provide methods and/or apparatus for chest x-ray imaging using technique settings that reduce patient exposure and/or provide improved contrast for lung tissue.

These objects are given only by way of illustrative example, and such objects may be exemplary of one or more embodiments of the invention. Other desirable objectives and advantages inherently achieved by the disclosed invention may occur or become apparent to those skilled in the art. The invention is defined by the appended claims.

According to one aspect of the invention, there is provided a method for obtaining a digital chest x-ray image. The method provides a default set of technique settings for the chest x-ray, wherein the default set is selectable by an operator command and includes using a peak kilovoltage exposure setting that is below 90 kVp with beam filtration of the x-ray and applying a rib contrast suppression algorithm to digital chest x-ray image data acquired from the exposure.

BRIEF DESCRIPTION OF THE DRAWINGS

The foregoing and other objects, features, and advantages of the invention will be apparent from the following more particular description of the embodiments of the invention, as illustrated in the accompanying drawings. The elements of the drawings are not necessarily to scale relative to each other.

DETAILED DESCRIPTION OF THE INVENTION

Figure 1:
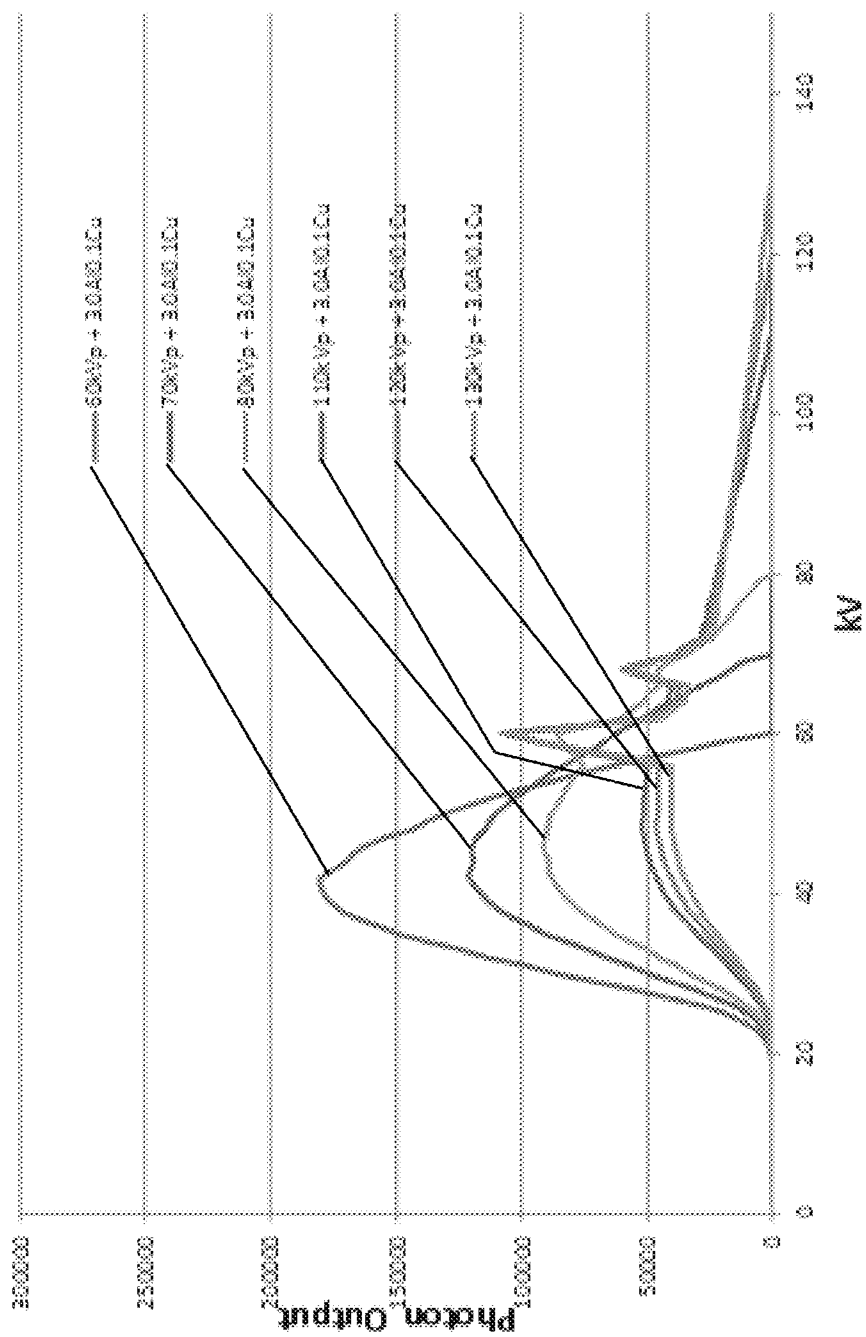
FIG. 1 is a graph that shows photon output for x-ray energy at different kVp levels.

This application claims priority to U.S. Provisional Ser. No. 61/616,455, filed Mar. 28, 2012 in the names of Xiaohui Wang et al. entitled "CHEST RADIOGRAPHY IMAGE CONTRAST AND EXPOSURE DOSE OPTIMIZATION", incorporated herein by reference in its entirety.

Reference is made to U.S. application Ser. No. 13/527,629 entitled "Rib Suppression in Radiographic Images" to Huo, incorporated herein by reference in its entirety.

The following is a detailed description of exemplary embodiments of the invention, reference being made to the drawings in which the same reference numerals identify the same elements of structure in each of the several figures.

In the context of the present disclosure, a digital chest x-ray can be obtained from a digital receiver (DR) or computed radiography (CR) receiver.

In the context of the present disclosure, the terms "viewer", "operator", and "user" are considered to be equivalent and refer to the viewing practitioner, technician, or other person who views and manipulates an x-ray image, such as a fluoroscopic image, on a display monitor. A "viewer instruction" or "operator command" can be obtained from explicit commands entered by the viewer or may be implicitly obtained or derived based on some other user action, such as making a collimator setting, for example. With respect to entries on an operator interface, such as an interface using a display monitor and keyboard, for example, the terms "command" and "instruction" may be used interchangeably to refer to an operator entry.

Digital radiography allows the improvement or optimization of image capture, processing, and presentation as separate steps in the imaging chain. It would be desirable, wherever possible, to capture a single digital chest radiograph and to process its image data differently depending on the type of tissue that needs to be examined. It would be of particular value if this could be accomplished with reduced effective patient dose from that used in conventional practice.

Exemplary method and/or apparatus embodiments of the application are directed to obtaining chest x-ray images and acquiring image data using a set of x-ray setup parameters, also termed techniques that differ in ways from those conventionally used in chest radiography, but that improve imaging of the lung parenchyma with reduced dose to the patient. The parameter set provides exposure at levels below those conventionally used for chest x-ray imaging and can automatically apply tools that compensate for high rib contrast that would otherwise require higher exposure.

A factor that has caused radiography personnel to use higher peak kilovoltage (expressed as kV or kVp) levels than are optimal for imaging the lung parenchyma relates to reduced rib contrast.

In at least one aspect of a method embodiment described herein, there can be used a rib contrast suppression process described in U.S. Ser. No. 13/527,629 entitled "Rib Suppression in Radiographic Images" to Huo, incorporated herein by reference. In the process, a lung segmentation process is followed by a rib detection process in which rib content is separated from non-rib image content. A rib labeling step follows, with classification of the rib content, grouping likely rib pixels into corresponding categories and helping to remove false positives. Some amount of prior knowledge of rib structures, such as shape and general direction, is used, along with morphological filtering. Characteristics such as gradient orientation and shape are used for rib edge segmentation, in which edge portions of the ribs are identified. Finally, rib subtraction is used to subtract rib edges from the chest x-ray image to provide a rib-suppressed x-ray image.

It is noted that alternate methods for rib contrast suppression for acquired data can be used, including those using modeling or based on other features. Rib contrast suppression, when properly applied, helps to reduce the impact of rib structures on the surrounding tissue, so that the lung parenchyma can be more readily visible. Using rib contrast suppression allows the reduction of kVp levels used for imaging, so that values lower than 120 kVp can be used to provide a suitable chest x-ray image. This helps to reduce overall noise levels, improving image contrast.

Applicants have recognized that the separation of image acquisition, processing, and presentation in the radiographic imaging chain can be used to provide images of both rib structure and lunch parenchyma from a single PA (posteroanterior) or AP (anteroposterior) chest x-ray image that is obtained at a lower exposure than is conventionally employed. By appropriate use of digital image processing algorithms to selectively enhance or suppress certain anatomical features for different diagnostic purposes, the need to acquire separate images using different exposures at the expense of increased patient dose can be reduced or eliminated in many cases.

Another consideration for improving or optimizing dose relates to reducing the amount of energy absorbed by patient tissue. Radiation at lower frequencies is absorbed at higher levels by human tissue. In general, higher energy photons penetrate and pass through the imaged subject more effectively and are less likely to be absorbed than are photons of lower energy. For this reason, conventional practices for chest imaging of adults set energy levels above or well above 90 kVp.

To counteract effects of increased absorbed patient dose and beam hardening, embodiments of the present method define low kV beam spectra optimized based on different patient body habits. This can be achieved using a combination of kVp selection, beam filtration materials and thickness, under the constraint of patient dose efficiency (e.g., image quality vs. patient absorbed dose).

The graph of FIG. 1 shows relative photon output, for exposure at standard kVp settings, at different energy levels. At a setting of 60 kVp, for example, photon output peaks for photon energies center about 40 kV, with a dramatic decrease in photon output at higher energies. There is very little energy above 60 kV. At 130 kVp, on the other hand, photon output energy has a much broader distribution, with a significant amount of energy above 60 kV.

At lower kVp settings, a higher proportion of the radiant energy is absorbed. Exemplary embodiments of methods can apply filtering to reduce the photon output at lower kV values, while still using lower kVp settings.

Figure 2:
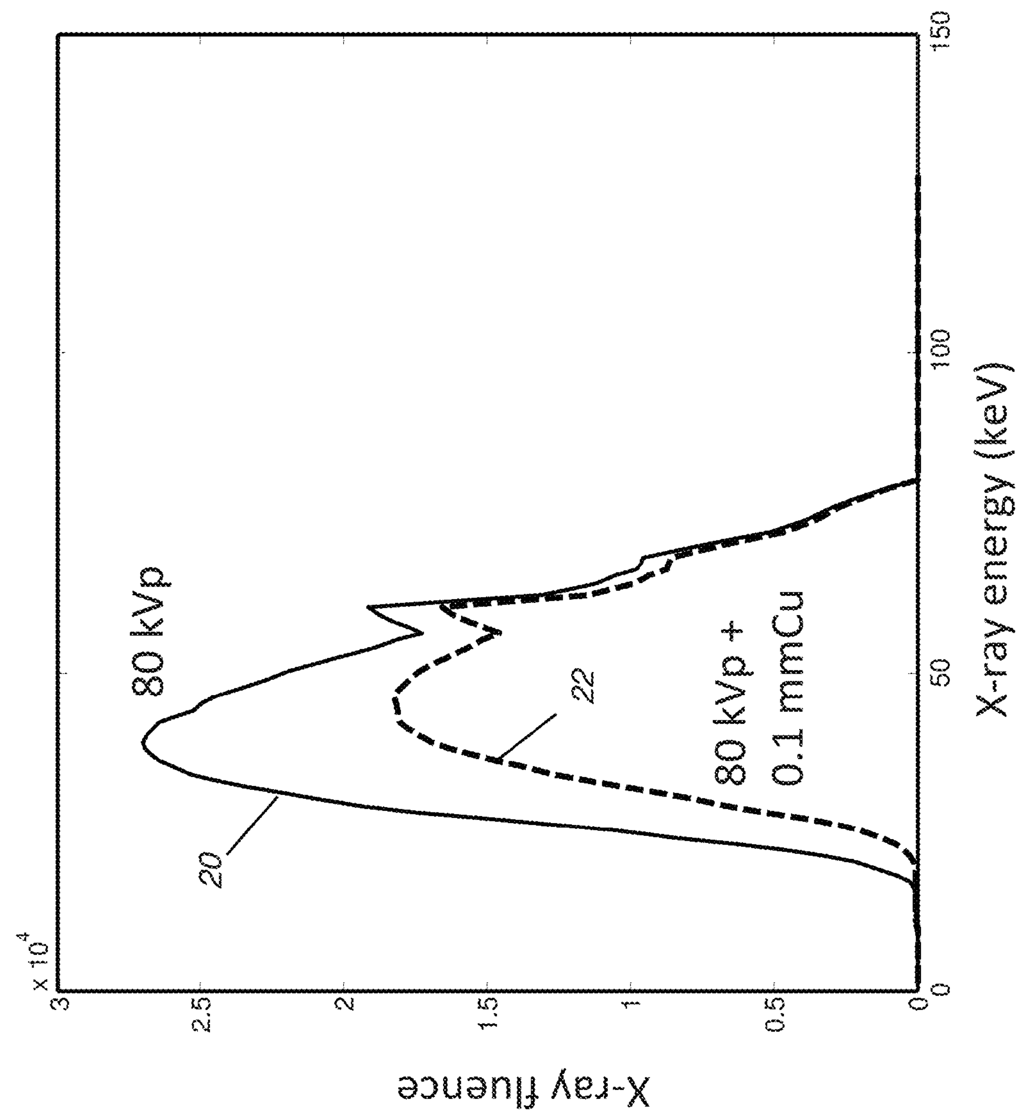
FIG. 2 is a graph that shows the net effect of filtration on energy level at a lower kV.

The graph of FIG. 2 shows how filtration can be used to modify the relative energy distribution for an 80 kVp curve 20 from FIG. 1. A filtration curve 22 is shown, reducing the number of lower energy photons provided. Filtration is provided by a filter that is coupled to the x-ray source and is inserted into the path of the emitted radiation, typically in an automated manner, using procedures familiar to those skilled in the radiography arts. Filtration is generally expressed in terms of a thickness of metal, such as filtration equivalent to millimeters (mm) of copper (Cu) or aluminum (Al).

Applicants have recognized the need to provide an accessible way to implement chest x-ray setup that allows the use of lower kVp settings and compensates for photon energy absorption levels using filtration and for bone structures using rib contrast suppression. Settings of lower than 90 kVp have been found to provide acceptable results, when combined with rib contrast suppression and filtering of about 0.1 mm Cu.

Figure 3A:
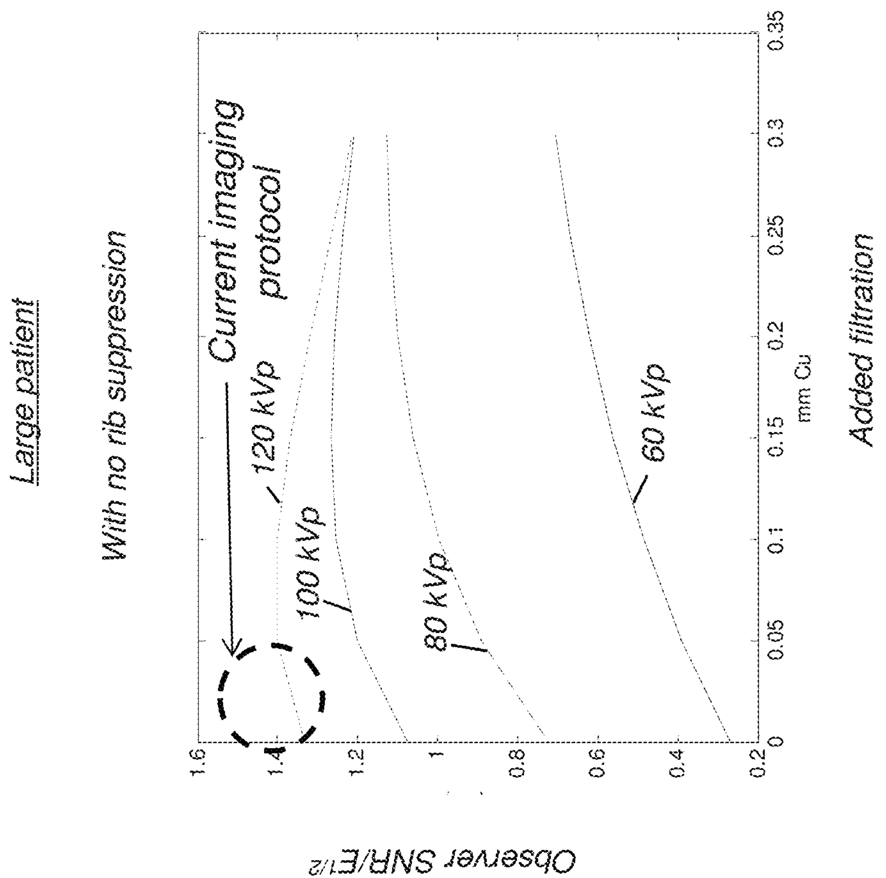
FIGS. 3A and 3B are graphs that show conventional and new image protocol for a large adult patient.
Figure 3B:
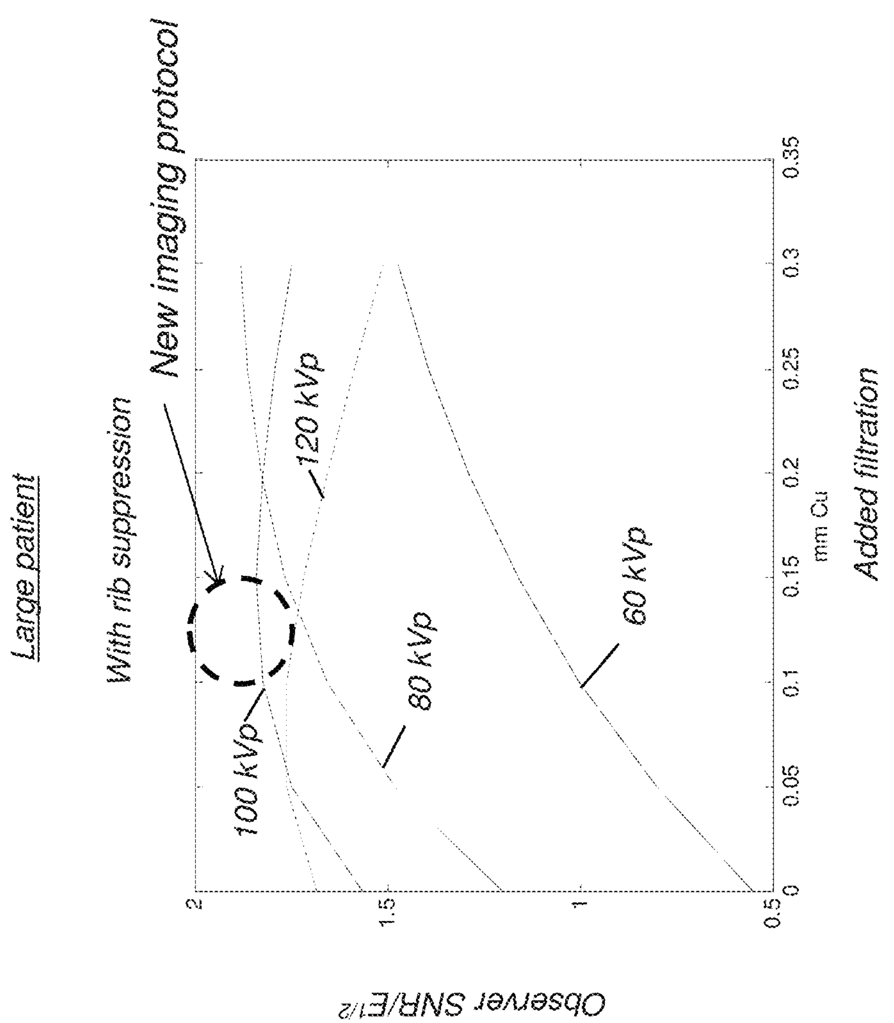

FIGS. 3A and 3B show the performance of a model human observer for viewing a 5 mm lung nodule in a large adult patient (generally, patients weighing about 180 lbs. or more). In the graph of FIG. 3A, conventional imaging protocol is used, with exposure at 120 kVp and without rib contrast suppression applied. As can be seen for conventional protocol with 120 kVp exposure, as outlined within the dashed circle, observer signal-to-noise ratio/(effective dose)$^{1/2}$(SNR/E$^{1/2}$) peaks at about 1.4, with no filtration or with a modest amount of added filtration. As FIG. 3B shows, the use of rib contrast suppression algorithms changes the SNR/E$^{1/2}$ characteristic. A new imaging protocol uses 100 kVp and added filtration of between about 0.1 and 0.15 mm Cu for the same sized patient, and provides an improved observer SNR/E$^{1/2}$ value approximating 1.8. In FIGS. 3A-3B, observer SNR/E$^{1/2}$s can provide an image quality benchmark shown using consistent arbitrary image quality unit values.

Figure 4A:
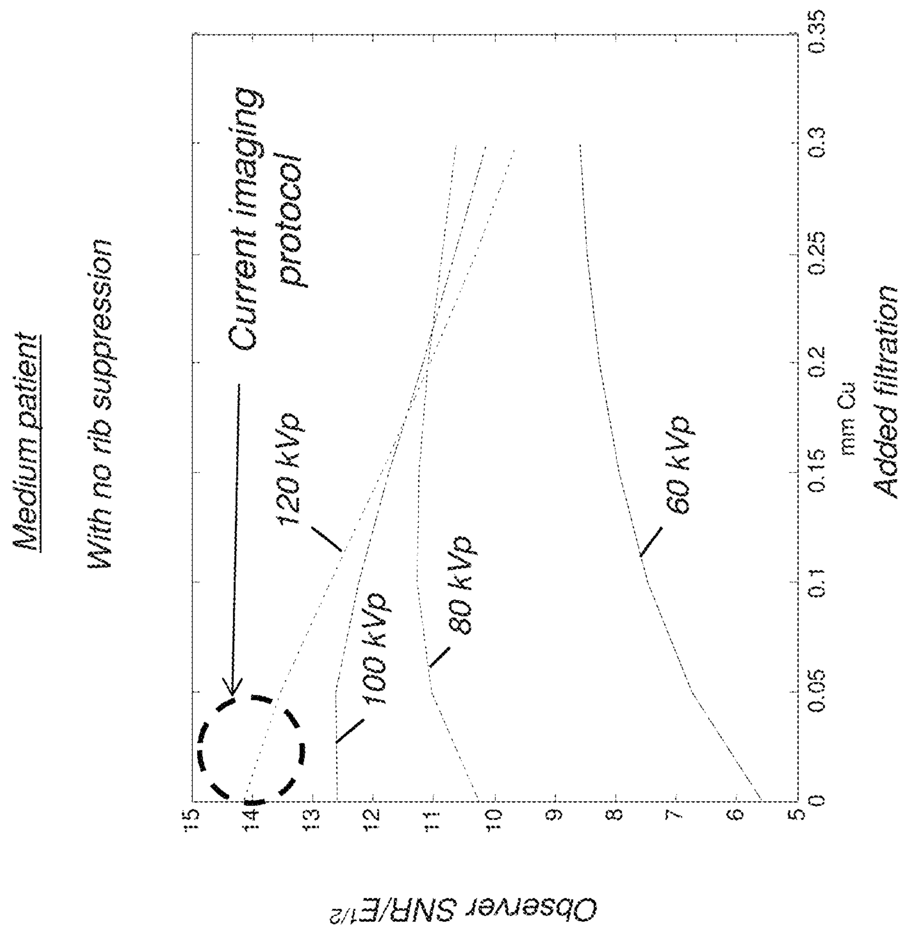
FIGS. 4A and 4B are graphs that show conventional and new image protocol for a medium-sized adult patient.
Figure 4B:
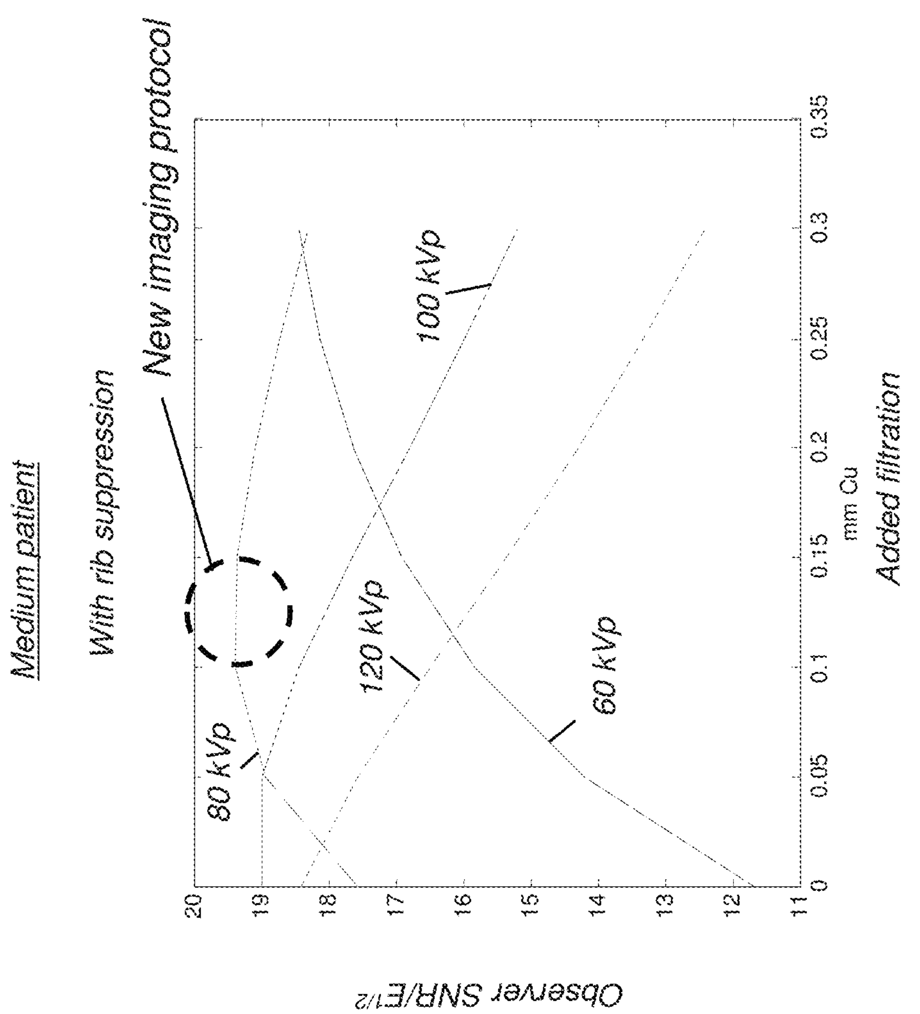

FIGS. 4A and 4B show the performance of a model human observer for viewing a 5 mm lung nodule in a medium-sized adult patient (generally, patients weighing between about 150-180 lbs.) In the graph of FIG. 4A, conventional imaging protocol is used, with exposure at 120 kVp and no rib contrast suppression applied. As noted for conventional protocol with 120 kVp exposure, as outlined within the dashed circle, observer signal-to-noise ratio (SNR) can be normalized by the dose or effective dose (E), for example SNR/E$^{1/2}$, peaks at about 14, with no filtration or with very little added filtration. As FIG. 4B indicates, the use of rib contrast suppression algorithms changes the normalized observer SNR characteristic significantly. According to an embodiment of this application, a new imaging protocol can use a reduced energy level with a peak kilovoltage exposure setting of 80 kVp and added filtration of between about 0.1 and 0.15 mm Cu, and/or can provide an improved observer SNR/E$^{1/2}$ value approximating 19.5. In FIGS. 4A-4B, observer SNR/E$^{1/2}$s can provide an image quality benchmark shown using consistent arbitrary image quality unit values.

Figure 5A:
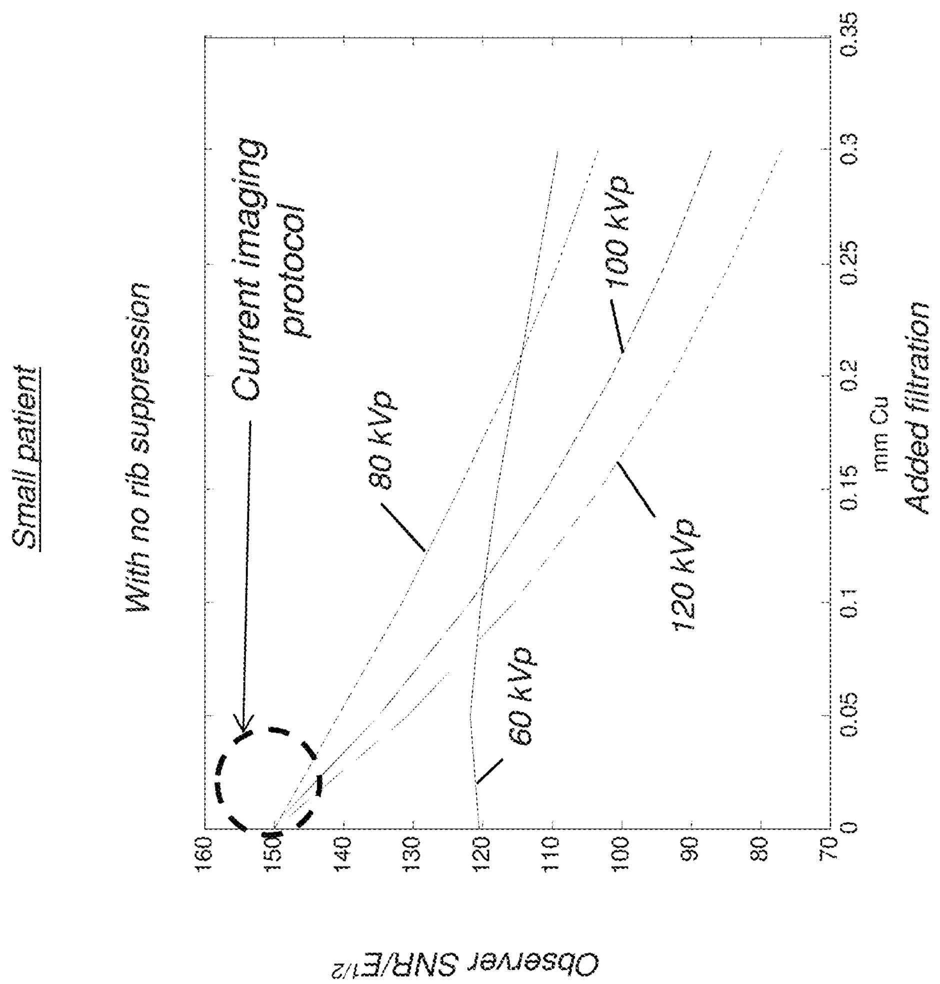
FIGS. 5A and 5B are graphs that show conventional and new image protocol for a small adult patient.
Figure 5B:
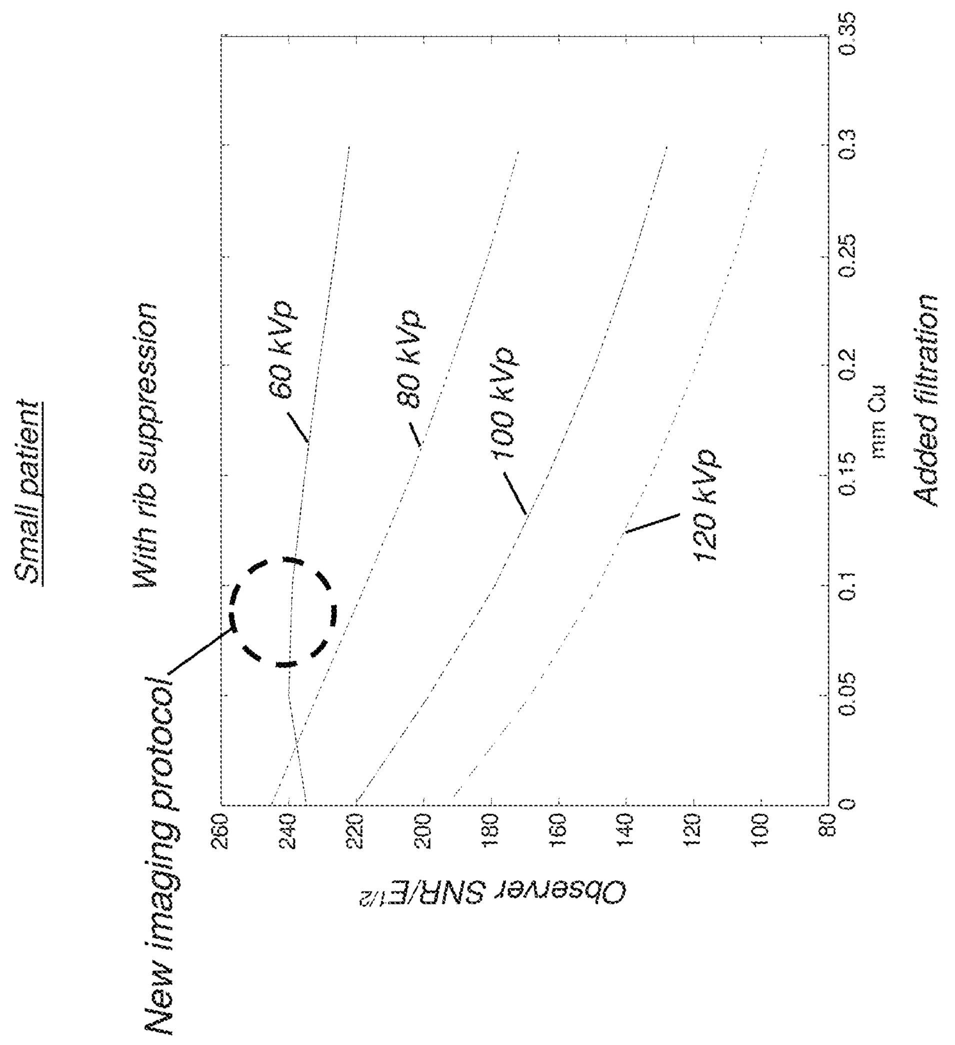

FIGS. 5A and 5B show the performance of a model human observer for viewing a 5 mm lung nodule in a small adult patient (generally, patients weighing between about 110-150 lbs.) In the graph of FIG. 5A, conventional imaging protocol is used, with exposure at 120 kVp and no rib contrast suppression applied. As noted for conventional protocol with 120 kVp exposure, as outlined within the dashed circle, observer signal-to-noise ratio (SNR)/(effective dose$^{1/2}$) (SNR/E$^{1/2}$) peaks at about 150, with no filtration or with very little added filtration. As FIG. 5B illustrates, the use of rib contrast suppression algorithms changes the SNR/E$^{1/2}$ characteristic significantly. According to one exemplary method embodiment of this application, an imaging protocol uses a reduced energy level with a peak kilovoltage exposure setting of 60 kVp and added filtration of about 0.1 mm Cu, and provides an improved observer SNR/E$^{1/2}$ value approximating 240. In FIGS. 5A-5B, observer SNR/E$^{1/2}$s can provide an image quality benchmark shown using consistent arbitrary image quality unit values.

As FIGS. 3B, 4B, and 5B illustrate, the use of rib contrast suppression on the acquired image data allows lower kVp levels to be used for adults in each size category and, in each case, improves with filtration at appropriate levels. Filtration can help to reshape the spectral profile of the x-ray beam and/or reduce the amount of radiation that is absorbed in the patient's tissue. In one embodiment, an improvement in observer SNR/E$^{1/2}$ with rib suppression can be at least 10%, at least 20% or more than 50% over conventional chest imaging techniques. As shown in FIG. 3B an improvement in observer SNR/E$^{1/2}$ with rib suppression is 29%, a 38% improvement in FIG. 4B, and a 60% improvement in FIG. 5B.

Figure 6A:
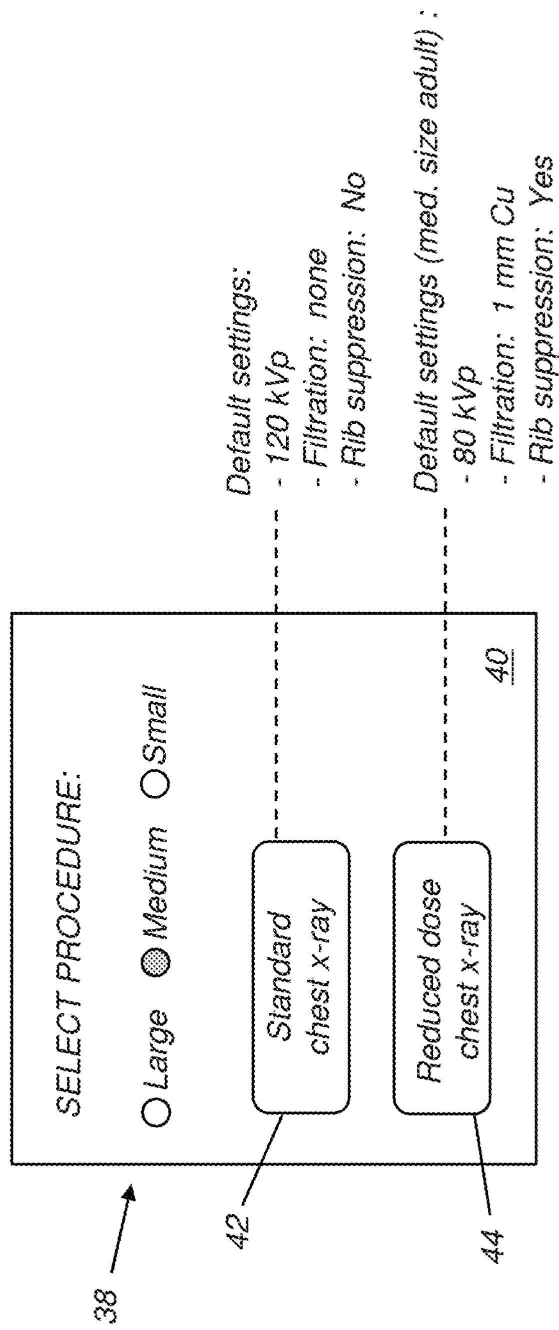
FIG. 6A is a plan view that shows an operator interface for selection of improved settings for chest x-rays according to an embodiment of the present invention.

One consideration with implementing the exposure values relates to conventional practices and workflow. FIG. 6A shows a plan view of an operator interface screen 40 that interacts with a radiography system and allows the technician to select, with entry of a single command, a desired standard or reduced-dose procedure for chest x-ray settings. These sets of settings specify technique settings that determine the radiation conditions under which the image data is acquired, and also the image processing that is used.

A group of controls 38 allow the operator to specify relative patient size. A control button 42 enters an operator instruction to use the conventional set of default settings for chest x-ray use. An alternate control button 44 sends an operator instruction to use the set of technique and process settings made available using lower kVp with filtering and rib contrast suppression. Typical default parameter settings for the different control button selections are shown.

In an alternate embodiment, the operator has the option to adjust any of the settings shown. Thus, for example, the operator could select the set of standard chest x-ray technique settings with control button 42, but change the default settings to select rib contrast suppression. The default setting for filtration provides a signal to the imaging apparatus to employ a filter of a suitable thickness, typically given in mm copper (Cu) or equivalent to a thickness of copper. This filter is then automatically deployed by the imaging apparatus.

Figure 6B:
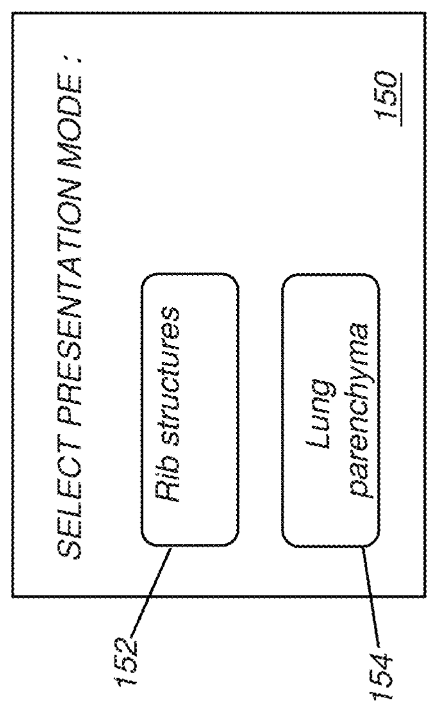
FIG. 6B is a plan view that shows an operator interface for selection of a presentation mode for a reduced-dose image obtained according to an embodiment of the present invention.

An additional input interface screen 150, as shown in FIG. 6B, has controls 152 and 154 that enable operator command selection of a presentation mode for the image that is obtained, either for showing rib structures or, using rib contrast suppression algorithms, for showing lung parenchyma. If neither mode is selected, both images are shown, that is, one image without rib contrast suppression that provides enhanced bone contrast and another image with rib contrast suppression for enhanced parenchyma contrast.

Figure 7B:
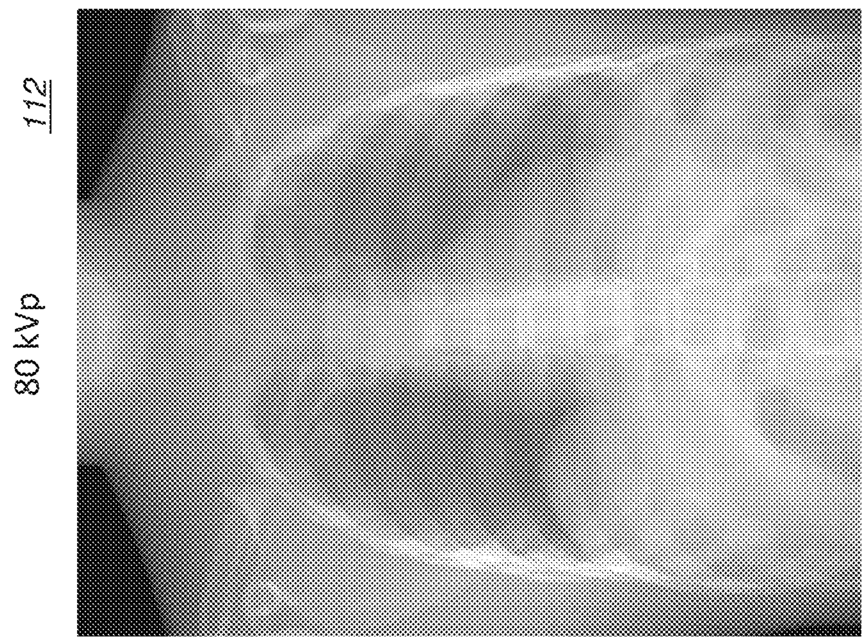
FIG. 7B shows a portion of a chest x-ray that has been obtained using lower peak kilovoltage exposure settings, but without rib contrast suppression.
Figure 7A:
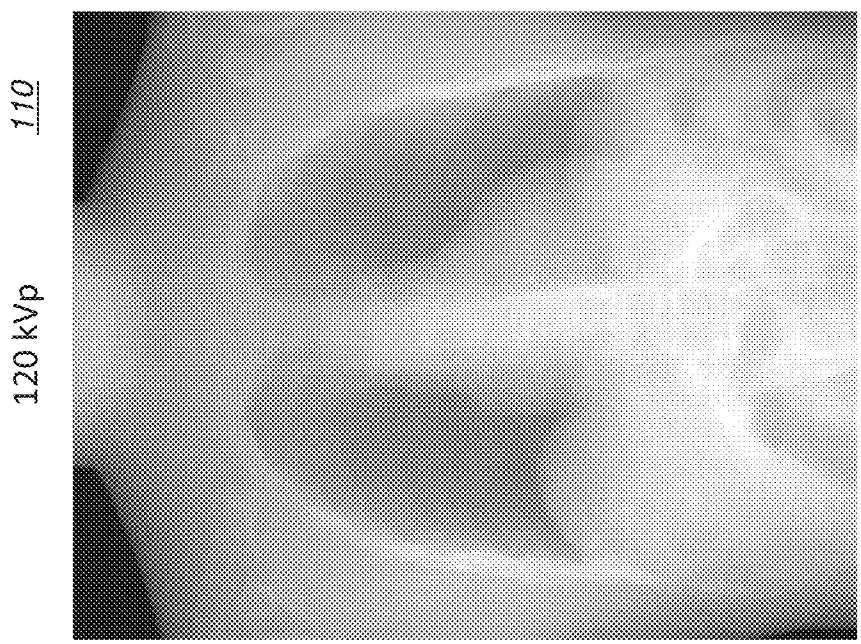
FIG. 7A shows a portion of a chest x-ray that has been obtained using conventional settings.
Figure 7C:
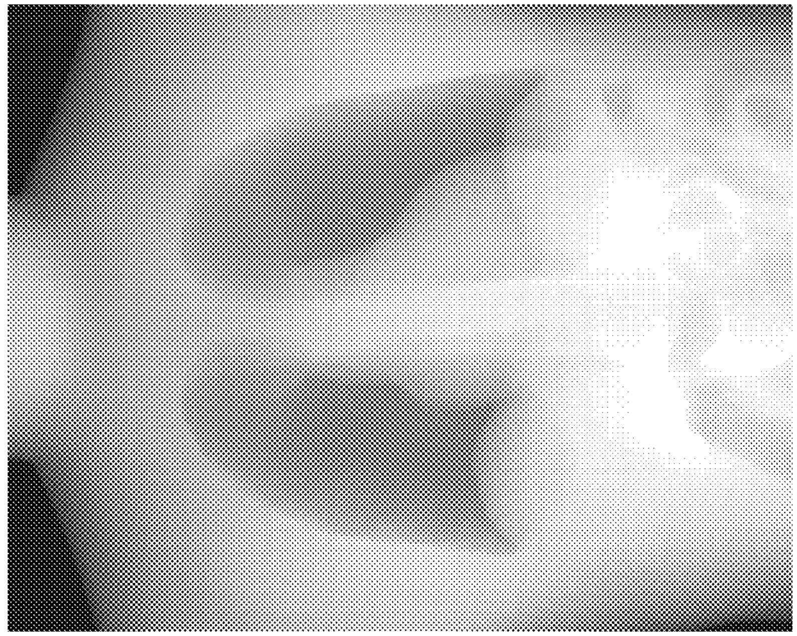
FIG. 7C shows a portion of a chest x-ray that has been obtained using lower peak kilovoltage exposure settings with rib contrast suppression according to an embodiment of the present invention.

By way of example, FIG. 7A shows a portion of a chest x-ray 110 that has been obtained using conventional settings, with energy levels set to 120 kVp. FIG. 7B shows a portion of the chest x-ray 112 using lower kVp settings, but without applying rib contrast suppression. FIG. 7C then shows the clearer contrast of an x-ray 114 that is obtained using the default reduced dose set with lower kVp settings, filtration, and rib contrast suppression for processing the obtained image data, as provided using embodiments of the present invention.

Figure 8:
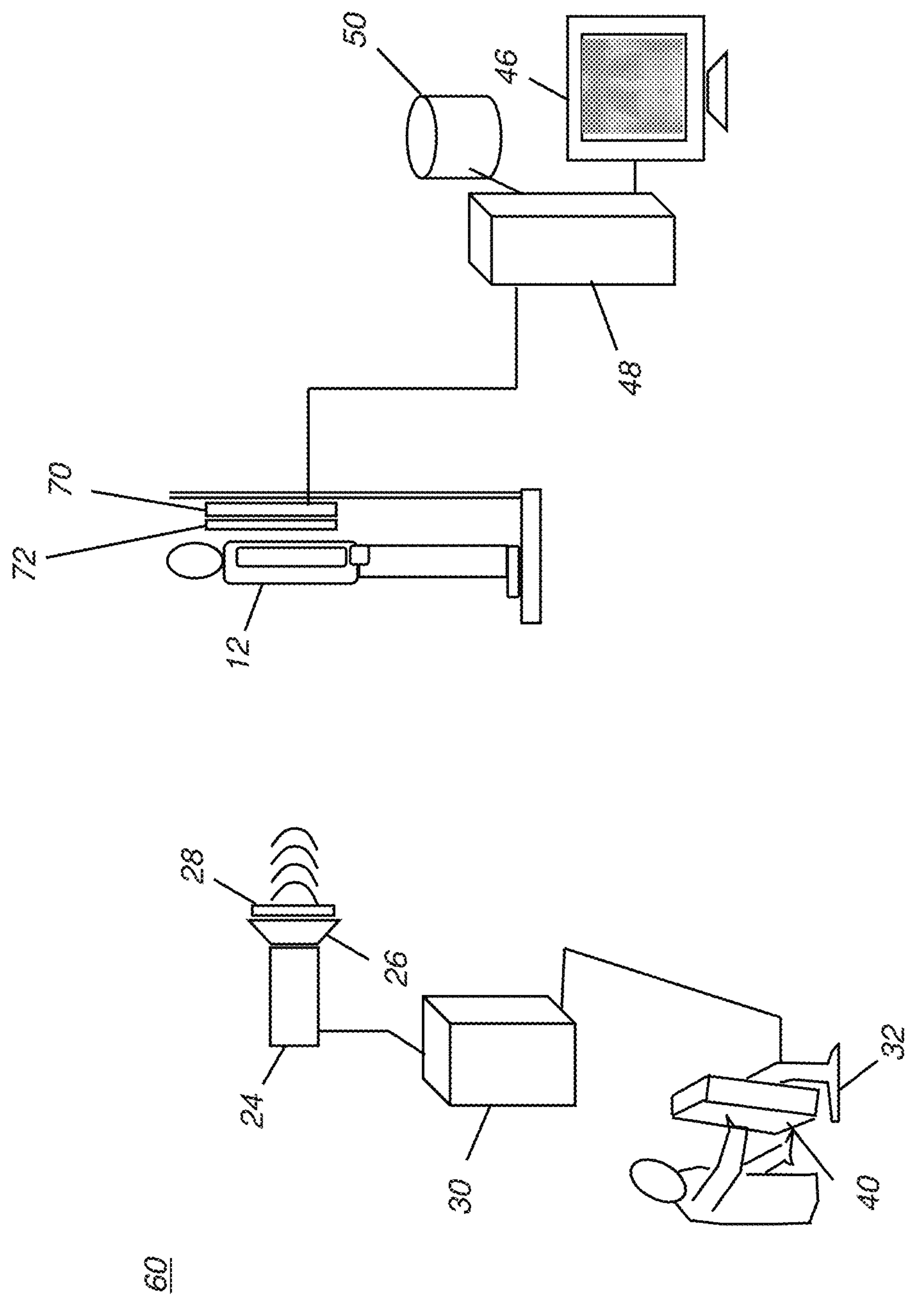
FIG. 8 is a schematic diagram of an imaging apparatus for providing chest x-ray imaging of a patient according to an embodiment of the present invention.

Referring to FIG. 8, there is shown a schematic diagram of an exemplary imaging apparatus 60 for providing chest x-ray imaging of a patient 12 according to an embodiment of this application. An x-ray tube 24 provides the exposure radiation for imaging, under the control of control circuitry 30 that has an operator console 32 for entry of setup and operation commands from the technician. The operator console 32 can include a display 40 or other data entry devices for the technician. X-ray tube 24 has a collimator 26 that controls the angular and spatial distribution of radiation that is provided. A filter 28 can be provided at the output of x-ray tube 24. Filter 28 positioning is typically controlled by control circuitry 30. Imaging apparatus 60 uses a single DR detector 70 that can include a grid 72 for scatter compensation. A DR imaging processor 48 obtains the digital data from DR detector 70 and performs the image processing for the obtained image data, including but not limited to rib contrast suppression. A display 46 in communication with DR imaging processor 48, or other output device, then displays each obtained image. A computer-accessible memory 50 enables processing and storage of the obtained and processed image data.

Figure 9:
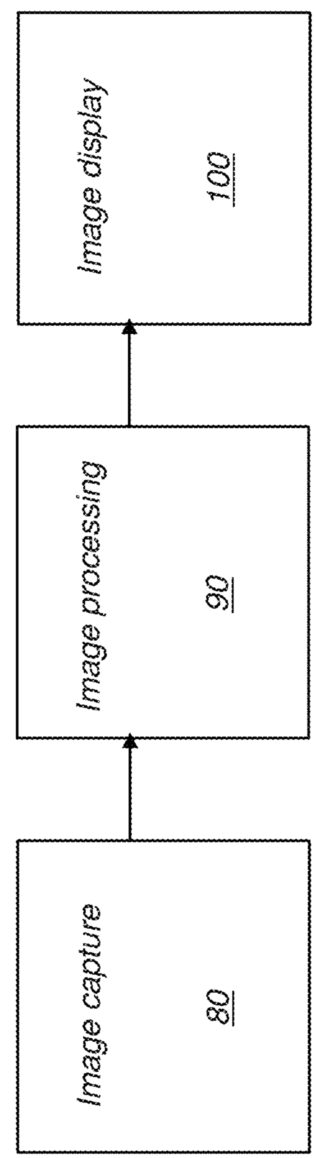
FIG. 9 is a schematic diagram that shows the process sequence that applies for digital radiography and is used in embodiments of the present invention that provide low-dosage chest x-rays.

The schematic block diagram of FIG. 9 shows an exemplary process sequence that applies for digital radiography and can be used in embodiments of this application that provide low-dosage chest x-rays. In image capture 80, a set of exposure settings includes a kVp setting that is lower than that conventionally used for acquiring image data for adult chest x-rays. In image processing 90, rib contrast suppression is applied to a copy of the acquired image data, allowing suppression of rib structures. In image display 100, as shown in FIGS. 7A and 7B, both a rib-suppressed image and an image without rib contrast suppression are available for the practitioner.

Advantageously, certain exemplary embodiments herein can provide the x-ray technician with settings and automated processing that are advantaged over the settings that are conventionally used for this purpose, without requiring the operator to specify options and settings that work together to compensate for lower energy radiation. Rib contrast suppression algorithms can be automatically applied to obtained images, so that the resulting image that is processed and displayed can provide detailed information for assessment of the lung parenchyma and other soft tissues within the chest region. Rib contrast suppression can be adjustable, so that the level of suppression is selectable by an operator.

Consistent with at least one embodiment, exemplary methods can use a computer program with stored instructions that perform on image data that is accessed from an electronic memory. As can be appreciated by those skilled in the image processing arts, a computer program of an embodiment of the present invention can be utilized by a suitable, general-purpose computer system, such as a personal computer or workstation. However, many other types of computer systems can be used to execute the computer program of the present invention, including an arrangement of networked processors, for example. The computer program for performing the method of the present invention may be stored in a computer readable storage medium. This medium may comprise, for example; magnetic storage media such as a magnetic disk such as a hard drive or removable device or magnetic tape; optical storage media such as an optical disc, optical tape, or machine readable optical encoding; solid state electronic storage devices such as random access memory (RAM), or read only memory (ROM); or any other physical device or medium employed to store a computer program. The computer program for performing the method of the present invention may also be stored on computer readable storage medium that is connected to the image processor by way of the internet or other network or communication medium. Those skilled in the art will further readily recognize that the equivalent of such a computer program product may also be constructed in hardware.

It should be noted that the term "memory", equivalent to "computer-accessible memory" in the context of the present disclosure, can refer to any type of temporary or more enduring data storage workspace used for storing and operating upon image data and accessible to a computer system, including a database, for example. The memory could be non-volatile, using, for example, a long-term storage medium such as magnetic or optical storage. Alternately, the memory could be of a more volatile nature, using an electronic circuit, such as random-access memory (RAM) that is used as a temporary buffer or workspace by a microprocessor or other control logic processor device. Display data, for example, is typically stored in a temporary storage buffer that is directly associated with a display device and is periodically refreshed as needed in order to provide displayed data. This temporary storage buffer can also be considered to be a memory, as the term is used in the present disclosure. Memory is also used as the data workspace for executing and storing intermediate and final results of calculations and other processing. Computer-accessible memory can be volatile, non-volatile, or a hybrid combination of volatile and non-volatile types.

It will be understood that computer program products of this application may make use of various image manipulation algorithms and processes that are well known. It will be further understood that exemplary computer program product embodiments herein may embody algorithms and processes not specifically shown or described herein that are useful for implementation. Such algorithms and processes may include conventional utilities that are within the ordinary skill of the image processing arts. Additional aspects of such algorithms and systems, and hardware and/or software for producing and otherwise processing the images or co-operating with the computer program product of the present invention, are not specifically shown or described herein and may be selected from such algorithms, systems, hardware, components and elements known in the art.

In addition, while a particular feature of an embodiment has been disclosed with respect to only one of several implementations or embodiments, such feature can be combined with one or more other features of the other implementations and/or other exemplary embodiments as can be desired and advantageous for any given or particular function. To the extent that the terms "including," "includes," "having," "has," "with," or variants thereof are used in either the detailed description and the claims, such terms are intended to be inclusive in a manner similar to the term "comprising." The term "at least one of" is used to mean one or more of the listed items can be selected. Further, in the discussion and claims herein, the term "exemplary" indicates the description is used as an example, rather than implying that it is an ideal.

The invention has been described in detail with particular reference to a presently preferred embodiment, but it will be understood that variations and modifications can be effected within the spirit and scope of the invention. For example, the rib contrast suppression techniques that are used can be selected from any of a number of types of rib contrast suppression algorithm that is described in the literature. The presently disclosed embodiments are therefore considered in all respects to be illustrative and not restrictive. The scope of the invention is indicated by the appended claims, and all changes that come within the meaning and range of equivalents thereof are intended to be embraced therein.

What is claimed is:

1. A method for obtaining a digital chest x-ray image of an adult patient, comprising:

providing a default set of technique settings for acquisition of image data from an x-ray exposure of the adult patient's chest, the default set being selectable by an operator command and includes using a peak kilovoltage exposure setting that is below 90 kVp with beam filtration of the x-ray;

Acquiring the image data of the adult patient's chest using the default set of technique settings;

applying a rib contrast suppression algorithm to the acquired image data to generate the digital chest x-ray image; and Displaying or storing the digital chest x-ray image.

2. The method of claim 1 wherein the exposure setting is no higher than about 80 kVp.

3. The method of claim 1 wherein the default set of technique settings can be edited following their selection.

4. The method of claim 1 wherein the chest x-ray image is an anteroposterior or posteroanterior.

5. The method of claim 1 wherein the filtration is at least equivalent to 0.1 mm copper.

6. The method of claim 1 wherein the default set of technique settings varies according to patient size.

7. A method for obtaining a digital chest x-ray image of an adult patient, comprising:

accessing an operator instruction that specifies default settings that include exposure at a peak kilovoltage setting that is at or below 90 kVp and filtration equivalent to 0.1 mm copper;

obtaining image data from an x-ray exposure of the adult patient's chest at the specified default settings; and displaying or storing images of the obtained image data with and without rib contrast suppression processing.

8. The method of claim 7 wherein the exposure peak kilovoltage setting is no higher than about 80 kVp.

9. The method of claim 7 further comprising accepting an operator selection that indicates a relative patient size and adjusting the peak kilovoltage setting and filtration level according to the size selection.

10. A method for obtaining a digital chest x-ray image for an adult patient, comprising:

providing filtration equivalent to at least 0.1 mm copper to an x-ray radiation source;

exposing the chest of the adult patient with exposure from the x-ray radiation source at a peak kilovoltage setting that is at or below 90 kVp to acquire the chest x-ray image;

displaying the acquired chest x-ray image;

processing the acquired x-ray image using rib contrast suppression to generate a rib contrast suppressed chest x-ray image; and displaying or storing the rib contrast suppressed chest x-ray image.

11. The method of claim 10 wherein the exposure peak kilovoltage setting is no higher than about 80 kVp.

12. The method of claim 10 wherein the chest x-ray image is an anteroposterior or posteroanterior.

13. The method of claim 10 further comprising accepting an operator instruction selecting a level for the rib contrast suppression.

* * * * *